US005569218A

United States Patent [19]
Berg

[11] Patent Number: 5,569,218
[45] Date of Patent: Oct. 29, 1996

[54] ELASTIC GUIDE CATHETER TRANSITION ELEMENT

[75] Inventor: Todd A. Berg, Lino Lakes, Minn.

[73] Assignee: SCIMED Life Systems, Inc., Maple Grove, Minn.

[21] Appl. No.: 195,222

[22] Filed: Feb. 14, 1994

[51] Int. Cl.[6] ............................................. A61M 25/00
[52] U.S. Cl. ..................... 604/282; 604/280; 604/264; 138/134; 138/138
[58] Field of Search ..................... 604/264, 280, 604/281, 282; 138/123–125, 137–139, 140, 141, 143–145, 153

[56] References Cited

U.S. PATENT DOCUMENTS

| | | |
|---|---|---|
| 3,416,531 | 12/1968 | Edwards . |
| 3,485,234 | 12/1969 | Stevens . |
| 4,385,635 | 5/1983 | Ruiz . |
| 4,636,346 | 1/1987 | Gold et al. ............................. 604/280 |
| 4,690,175 | 9/1987 | Ouchi et al. . |
| 4,735,620 | 4/1988 | Ruiz . |
| 4,838,879 | 6/1989 | Tanabe et al. ........................ 604/280 |
| 4,863,442 | 9/1989 | DeMello et al. ...................... 604/282 |
| 5,176,660 | 1/1993 | Truckai ................................. 604/282 |
| 5,221,270 | 6/1993 | Parker .................................. 604/282 |
| 5,222,949 | 6/1993 | Kaldany . |
| 5,234,416 | 8/1993 | Macaulay et al. . |
| 5,254,107 | 10/1993 | Soltesz . |
| 5,279,596 | 1/1994 | Castaneda et al. .................... 604/280 |
| 5,308,342 | 5/1994 | Sepetka et al. ....................... 604/264 |

FOREIGN PATENT DOCUMENTS

| | | |
|---|---|---|
| 0180348 | 5/1992 | European Pat. Off. . |
| 92/15356 | 9/1992 | WIPO . |

Primary Examiner—John D. Yasko
Assistant Examiner—Ronald K. Stright, Jr.
Attorney, Agent, or Firm—Luke R. Dohmen

[57] ABSTRACT

A guiding catheter for use in coronary angioplasty and other cardiovascular interventions which incorporates a transition element in the shaft of the device. The transition element which has a different flexibility than the sections immediately proximal and distal to it, creates a zone in the catheter shaft which is either more or less flexible than the rest of the shaft. The transition element allows a portion of the shaft to be made more rigid or more flexible, without changing the flexibility of the other portions of the shaft. The transition element also allows for a differential flexibilty to be added to the catheter shaft.

15 Claims, 8 Drawing Sheets

ELASTIC GUIDE CATHETER TRANSITION ELEMENT

BACKGROUND OF THE INVENTION

1. Field of the Invention

The present invention generally relates to the field of intravascular medicine and more specifically refers to the field of angioplasty catheters such as guiding catheters used for the placement of medical devices and radiopaque fluids within the body for treatment of vascular diseases.

2. Description of the Prior Art

The use of intravascular catheters for the treatment of cardiovascular disease is well known in the field of medicine. The need for a greater variety of devices to treat different types of circumstances has grown tremendously as the techniques for the use of such devices has progressed.

Prior art guiding catheters are generally comprised of a shaft which is hollow, defining an inner lumen. The shaft is generally comprised of two tubes congruent to each other with a support member therebetween. A hub is connected to the proximal end of the shaft to provide a means for connecting another device such as a syringe to inject fluids, or for providing a means to direct the device in order to place it within the vessel. A tip of a desired shape is provided at the distal end of the shaft.

An example of the prior art catheters as described above is located in U.S. Pat. No. 3,416,531, issued Dec. 17, 1968, to M. L. Edwards, for CATHETER, which describes a catheter constructed with a reinforcement layer to impart torsional rigidity without impairing the flexibility of the device in bending. U.S. Pat. No. 3,485,234, issued Dec. 23, 1969, to R. C. Stevens, for TUBULAR PRODUCTS AND METHOD OF MAKING SAME, discloses placing the stainless steel braid in between a first and a second plastic extrusion. U.S. Pat. No. 5,254,107, issued Oct. 19, 1993, to P. P. Soltesz, for CATHETER HAVING BRAID REINFORCED TRANSITIONAL TIP, discloses a catheter which is constructed of a first tube, a reinforcement member placed over the first tube, and two different polymer tubes placed over the reinforcement layer to create two sections having different flexibilities. PCT publication No. WO 92/15356, published Sep. 17, 1992, to Nita et al., for CARDIOVASCULAR CATHETER HAVING DISCRETE REGIONS OF VARYING FLEXIBILITY, also teaches a catheter which has varying flexibilities along its length.

In order for the physician to place the catheter at the correct location in the vessel, the physician must apply longitudinal and rotational forces. In order for the catheter to transmit these forces from the proximal end to the distal end, the catheter must be rigid enough to push through the blood vessel, but yet flexible enough to navigate the bends in the blood vessel. The catheter must also be torsionally rigid to transmit the applied torque. To accomplish this balance between longitudinal rigidity, torsional rigidity, and flexibility, there is often a support member added to the shaft. This support wire is often comprised of a metal braid or coil imbedded in the shaft. This support wire is often embedded in the shaft between the two layers of tubing that comprise the shaft.

A guiding catheter is guided through the aorta over the aortic arch and down to the ostium of the vessel which is to be treated. Therefore, it is advantageous to have the proximal section be rigid to transmit the forces applied, but to have the distal end more flexible to allow for better placement of the guide catheter. Having the distal section more flexible also creates a less traumatic section to the blood vessel. The distal end of the catheter is rotated, through the transmission of torque from the proximal end, until the tip of the guiding catheter is in the desired position. With the variations of different bend shapes available on the distal ends of these devices and with variations in patient anatomy, each device may need to be torqued more or less in order to correctly place it.

One problem that has surfaced is that as more flexible distal sections are placed on these catheters, the resistance to guide catheter back-out is reduced. Guide catheter back-out is when the guide dis-engages from its preferred positioning, thereby creating the need for the physician to re-position the guiding catheter. Many different guide catheter curve shapes have been designed to overcome this problem, with each giving different levels of support. However, as the flexibility of the distal most section is reduced, the tendency for back-out again increases.

It is possible to construct a device that is very rigid to obtain the correct amount of back-out support. However, the resulting device would be very traumatic to the patient's arteries due to its rigidity. Similarly, it is possible to construct a very flexible device to limit the trauma the device imparts to the blood vessels. However, the device then becomes too flexible and does not provide any back-out support.

Another problem that is seen in current devices is that devices are constructed such that they are equally flexible in all planes. That feature is not always desired.

SUMMARY OF THE INVENTION

The present invention overcomes the disadvantages associated with the prior art by providing a transition element in the material. The present invention allows for flexibility of a guiding catheter to be increased, while maintaining its ability to prevent guide catheter back-out. The present invention also allows for the rigidity of a guiding catheter to be increased in a discrete segment, thereby increasing the back-out resistance while maintaining the flexibility. The present invention provides a manner in which a device of varying flexibility may be made very inexpensively. The present invention also provides a manner in which differential flexibility may be imparted to a guide catheter.

In the preferred embodiment of the invention, the catheter shaft material is removed in the transition section. The outer tube of the shaft is removed down to the braid of the catheter. This is done by a grinding process. The removal of this material creates a band in which there is no material present. That band is then filled with a material having different physical properties than the material which was removed, thereby changing that section's properties.

If the filler material substituted in the band is a more flexible material, the transition section will have the flexibility of both the remaining inner tube layer, the braid, and the new outer material. It is clearly seen that while this catheter section becomes a new combination, it will still be more flexible than the sections immediately proximal and distal to it. If the filler material substituted in the band is a more rigid material, the combination of the materials in this transition section will be more rigid than the sections immediately proximal and distal to it.

DETAILED DESCRIPTION OF THE PREFERRED EMBODIMENT

Figure 1:
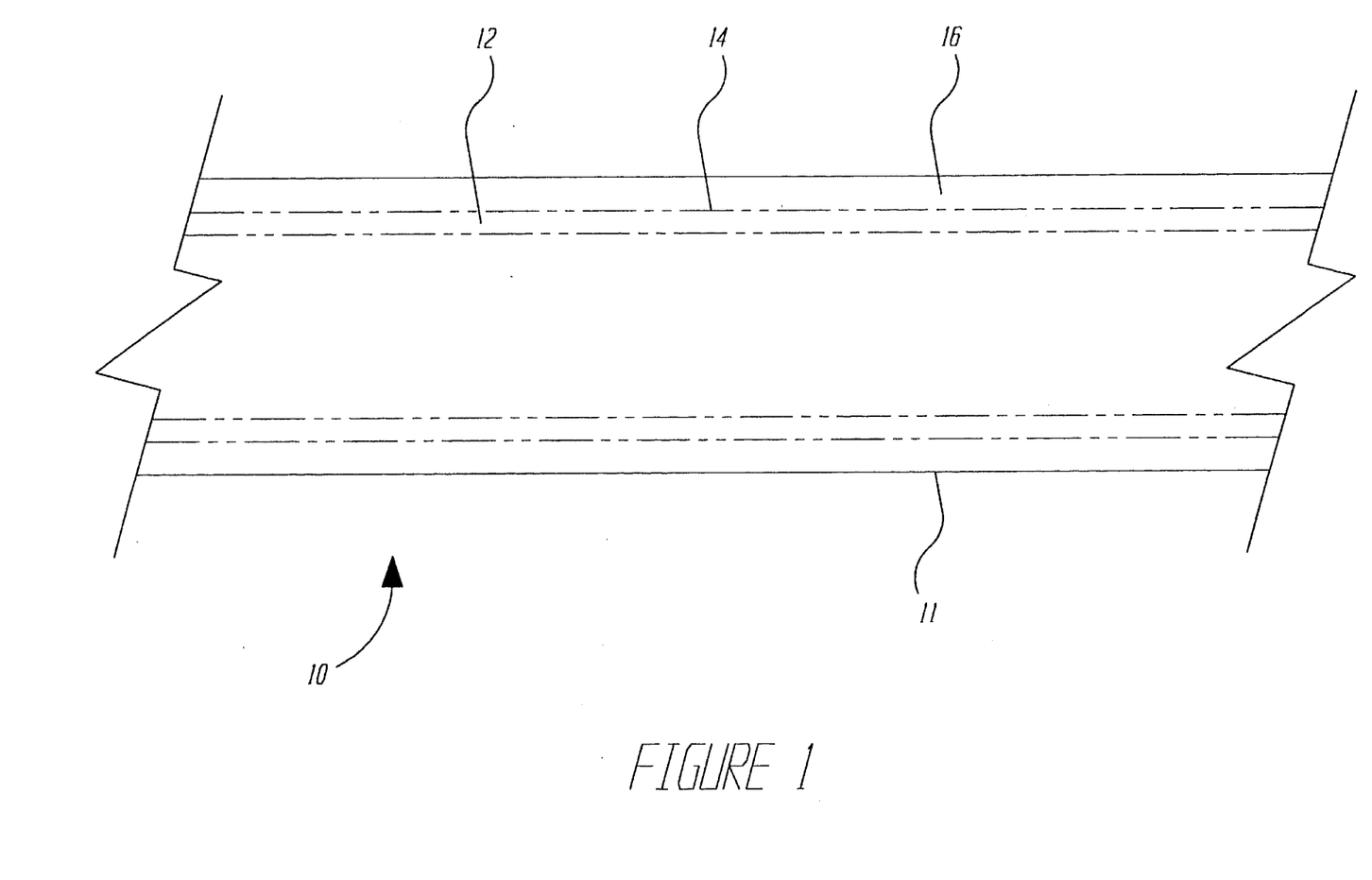
FIG. 1 is a plan view showing a section of the catheter shaft.

FIG. 1 shows a section of a catheter 10 which is preferably a guiding catheter. Catheter shaft 11 is comprised of an inner tube 12 which is surrounded by a support member 14. Support member 14 is then surrounded by an outer tube 16. Inner tube, 12 is represented in FIG. 1 by dashed lines and the support member 14 is represented by a dotted line.

Figure 6:
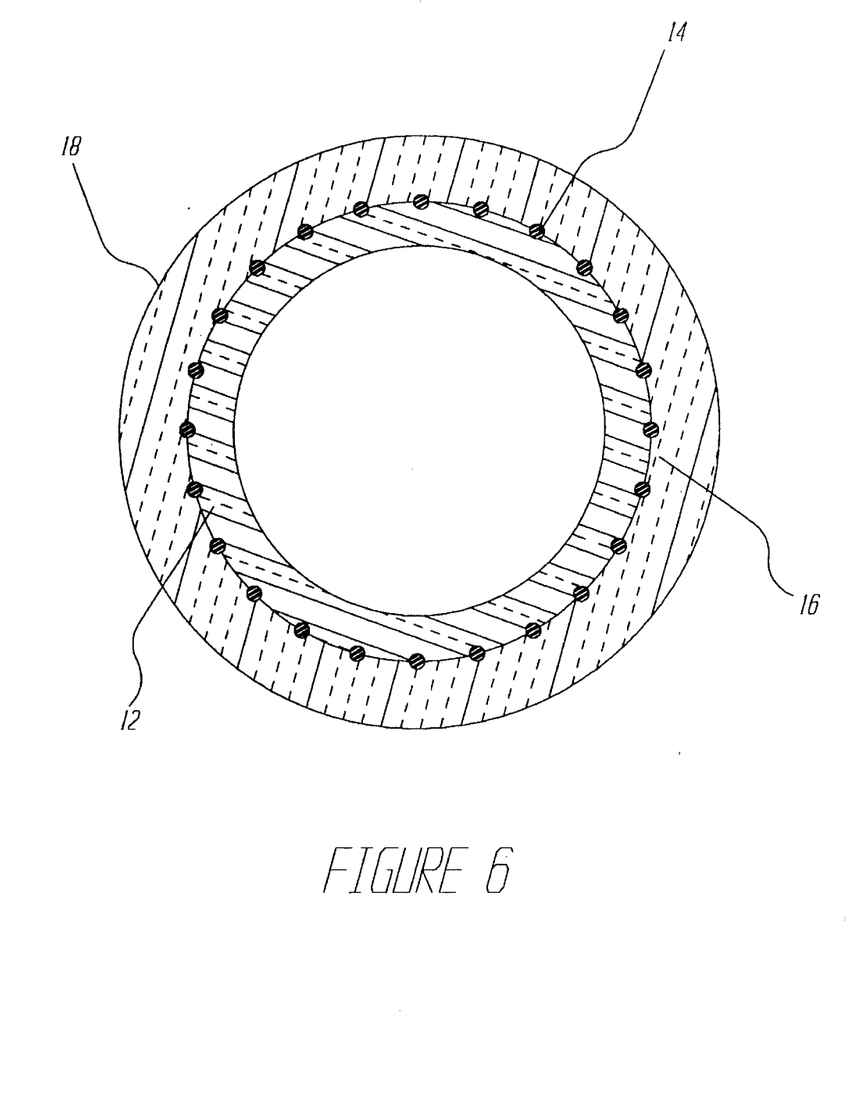
FIG. 6 is a cross section of FIG. 3 along line A—A.

In the preferred embodiment, inner tube 12 is a thin walled PTFE (polytetrafluoroethylene) tube. This creates a smooth, friction-free surface for the passage of other devices through the inner tube. Support member 14 is a 304 stainless steel wire, wound in a braided pattern around inner tube 12. Alternatively, support member 14 could also be comprised of polymer fibers. Outer tube 16 is a polymer jacket which is placed through an extrusion process onto combined layers of inner tube 12 and support member 14. Preferably outer tube 16 is comprised of PEBAX®, a polyether block amide (PEBA) available from ATOCHEM POLYMERS, Birdsboro, Pa. FIG. 6 shows a cross-section of this construction.

Figure 2:
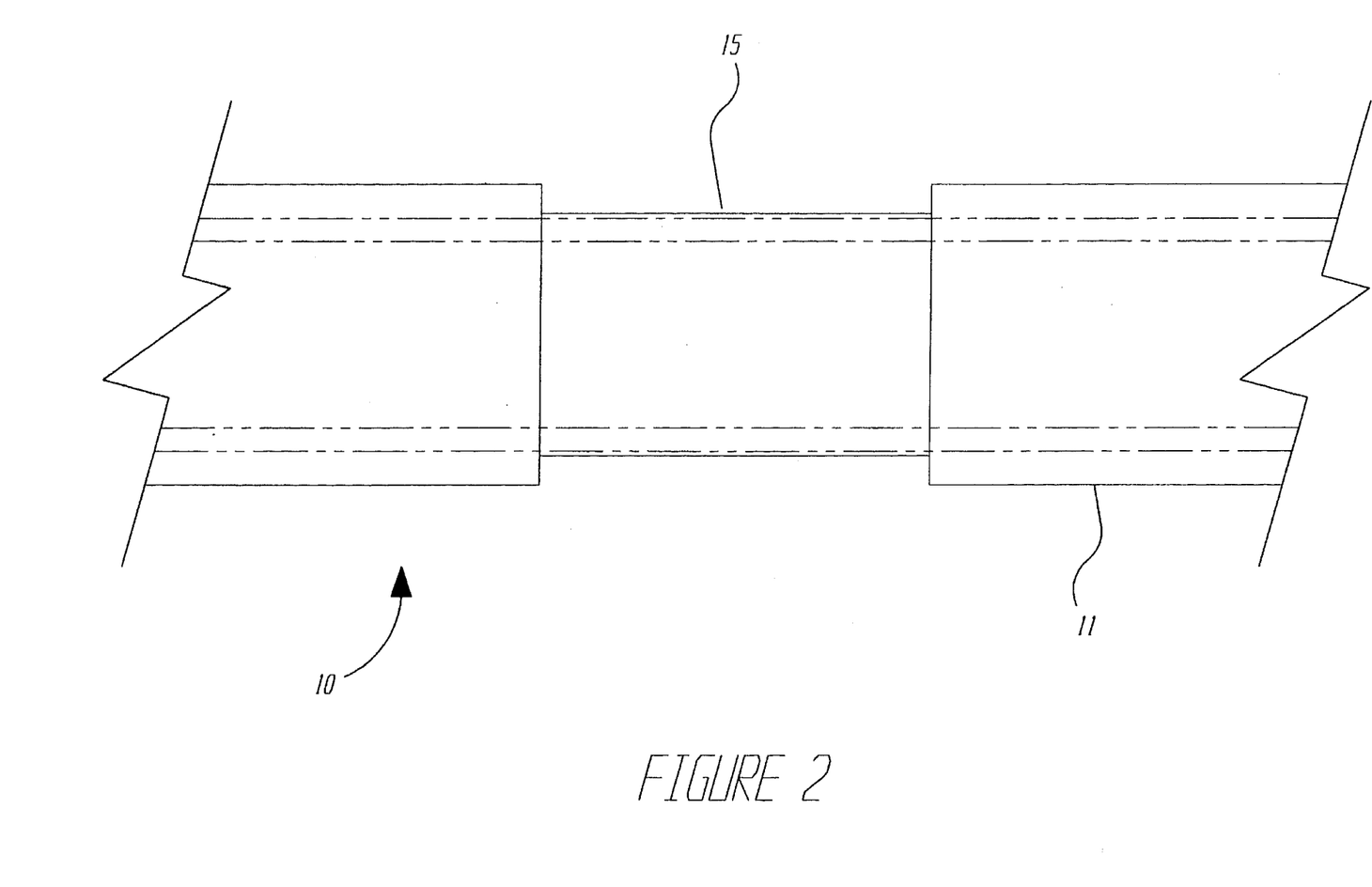
FIG. 2 is another plan view of the catheter shaft with a length of the shaft ground down to create a band.

FIG. 2 is a drawing of a portion of catheter 10. Catheter shaft 11 is shown having a section ground or abraded away to create a band 15 in which no material exists. As shown in FIG. 2, outer shaft 16 is removed to expose the support member 14, and to create a band 15 which will be filled later with a different material.

In the preferred embodiment, outer tube 16 is removed through an abrasion process. Specifically, the section in which the band 15 is wished to be created is brought in contact with a grinding wheel. Catheter shaft 11 is then rotated 360 degrees to remove material circumferentially around the device. The grinding wheel is slowly advanced to increase the depth of the cut, until the support member 14 is exposed. Although abrasion is the preferred mode of processing, the band 15 can be created in many different ways, some of which include alternate extrusion methods, cutting, and thermal processing.

Figure 3:
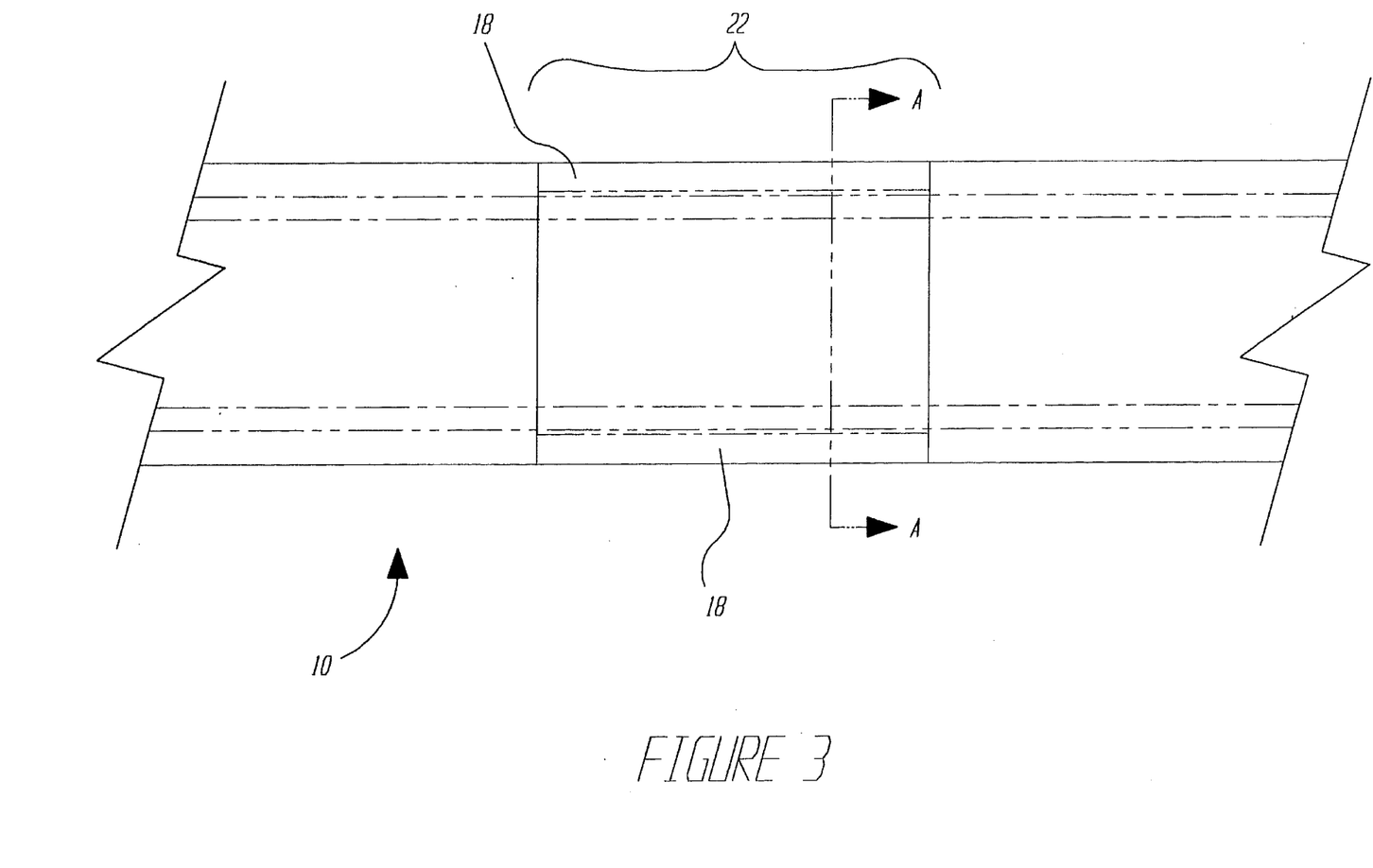
FIG. 3 is a plan view of FIG. 2 after the filler material has been added.

FIG. 3 is a plan view of the device depicted in FIG. 2 after the different material, filler material 18, has been placed in the band 15 to create the transition section 22. Filler material 18 is an element which has different physical properties than the outer tube 16. For example if the catheter shaft 11 is comprised of a flexible polymer, the filler material 18 may be a either a rigid polymer, a rigid metal, or an even more flexible polymer. Likewise, if the catheter shaft 11 is comprised of a rigid polymer, the filler material 18 may be a more flexible polymer material.

Filler material 18 is preferably a circular polymer tube with a diameter equal to the diameter of the band 15 and a length equal to the length of the band. The filler material 18 is cut longitudinally to allow it to be placed over the catheter shaft 11 and onto the band 15. A processing sleeve is then loaded over both the catheter shaft and the band. The entire transition section 22 is then subjected to a heating source to cause the materials to flow together. The processing sleeve allows for a smooth outer surface following thermal processing.

In the preferred embodiment the outer tube 16 is comprised of PEBAX having a durometer of 67 D. Although 67 D is preferred, the outer tube could be on the order of 40–70 D. The filler material 18 is also comprised of PEBAX but has a durometer of 35 D. Although 35 D is preferred, the outer tube could be on the order of 25–72 D. In the preferred embodiment, the band 15 length is in the order of 0.1 to 0.75 inches. The thickness of the band 15 varies with the amount of outer tube 16 material which is removed. For example, in an 8 F guiding catheter, the diameter of the outer tube is in the order of 0.102–0.106 inches. After the material is removed the diameter of the band 15 is on the order of 0.092–0.096 inches. The diameter of the catheter shaft 11, or outer tube 16, also varies with the desired end use for the product. A guiding catheter may be on the order of five to ten French, while a balloon angioplasty catheter will be on the order of two to five French.

Figure 4:
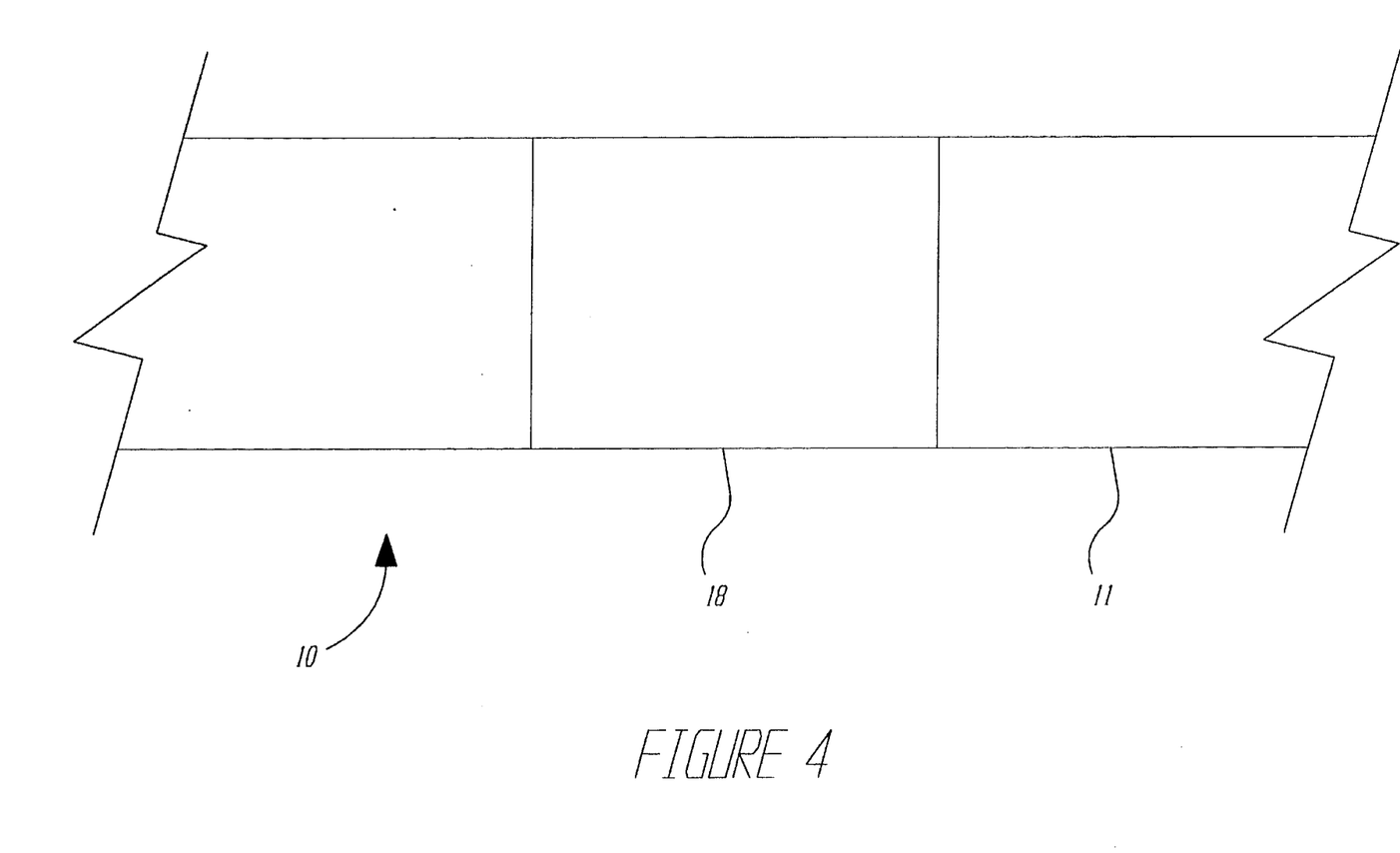
FIG. 4 is a perspective view of the catheter shaft of FIG. 3.

FIG. 4 shows the perspective view of the device when completed. Band 15 is replaced with filler material 18 in a circumferential pattern around the catheter shaft 11.

Figure 5:
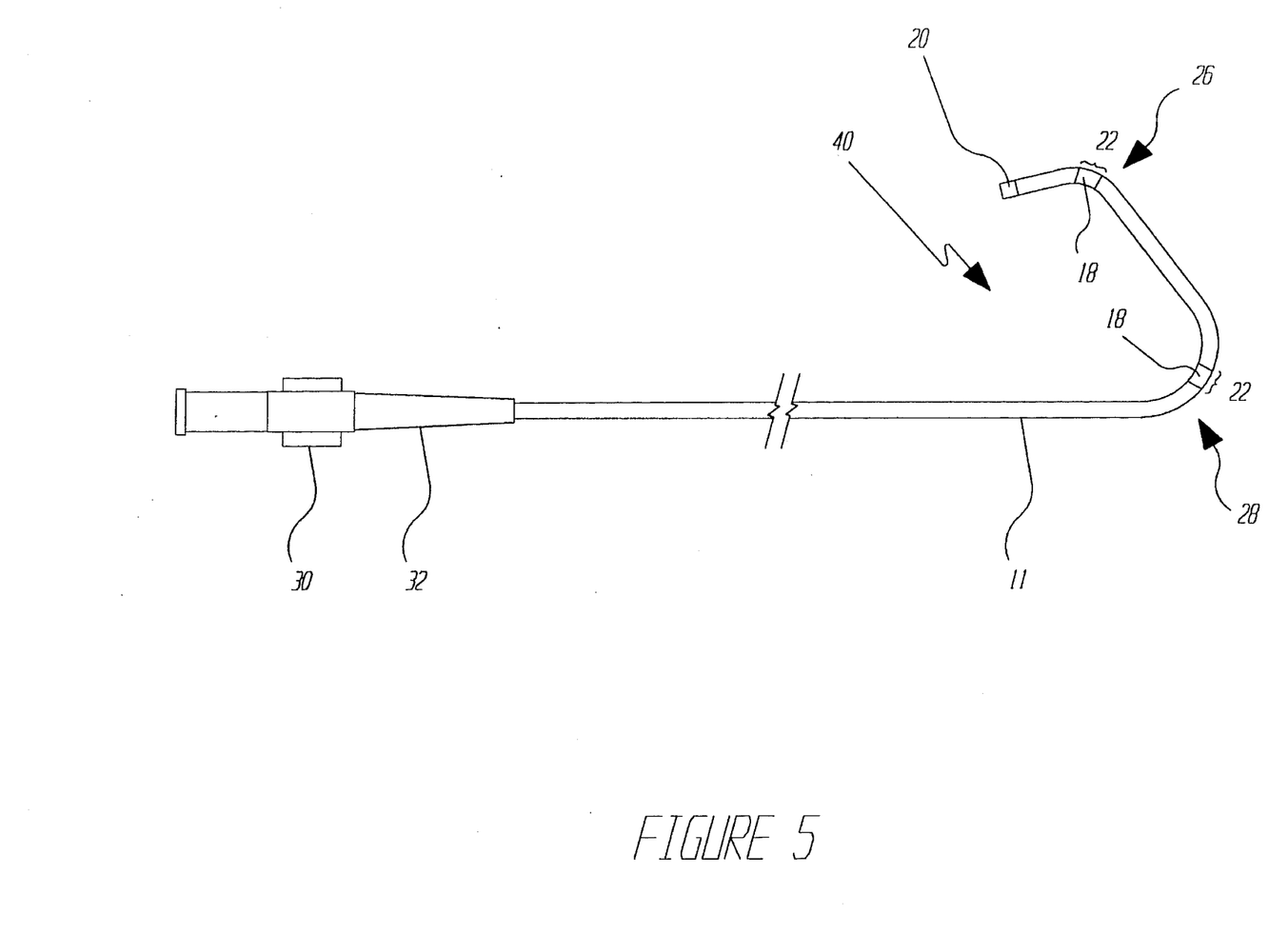
FIG. 5 is one embodiment of the present invention.

FIG. 5 shows a specific application of this invention in the area of guiding catheters. Guiding catheter 40 is comprised of a catheter shaft 11 which is constructed as described above. Connected to the proximal end of the catheter shaft 11 is a hub 30 and strain relief 32. The connection of these elements allows the physician to connect other devices to the guiding catheter 40 and to manipulate the device through the application of longitudinal or rotational forces. Connected to the distal end of the catheter shaft 11 is a distal tip 20. Distal tip 20 generally consists of a softer, more flexible polymer which is connected to the catheter shaft 11 through a thermal process. In the preferred embodiment, distal tip 20 is comprised of a PEBAX polymer tube having a durometer of 35–40 D. Distal tip 20 generally does not contain either the inner tube 12 or the support member 14. However, it is possible for these elements to be present in a portion of the distal tip 20.

The most distal section of the guiding catheter 40 is formed to correspond to a desired geometrical shape. This shape is determined by the specific anatomy of the patient, and the amount of guide catheter back-out support that is needed for the procedure. Generally, the guiding catheter has at least two bends at the distal end of the catheter shaft 11. These are the primary curve 26 and the secondary curve 28. These curves assist the physician in the placement of the device for treatment of the vessels.

In order to simultaneously maximize the amount of guide catheter back-out support and the flexibility of the distal end of the device, the present invention can be used. The present invention utilizes a catheter shaft which is relatively rigid, to provide for good guide catheter back-out support, and combines that with a filler material 18 which is relatively flexible. Therefore, a transition section 22 is created which is more flexible to allow for easier and less traumatic guide catheter placement. Flexible transition sections 22 can be located where tight radiuses are created due to the shape of the guide catheter to allow larger devices to pass through the curve with greater ease. The transition sections 22 act as elastic joints which better accommodate devices by allowing the shaft to straighten. In this embodiment, the transition sections 22 are created at the primary curve 26 or the secondary curve 28. This placement of the transition sections 22 provides the benefits of a flexible distal section and the benefits of a rigid distal section simultaneously. The transition sections 22 can be located strategically within the guide catheter shaft. Ideal locations include; a flexible transition section 22 at the primary curve radius to allow safer deep seating of the guide, flexible transition sections 22 at radius locations within the curve style to improve ease of device passage, and a rigid transition section 22 at the secondary curve to provide maximum back-out support.

Transition sections 22 can be applied to the main shaft in as many locations as needed. Because the support member 14 and the inner tube 12 are continuous through the transition section 22, a stronger bond is created. This is a key advantage over butt joints as described and used in the prior art. Most catheter shafts are made to be rigid the entire length of the catheter shaft to ensure the correct stiffness occurs at the desired locations. The catheter shaft does not need to be rigid the entire length to provide back-out support. The present invention allows for the rigidity or flexibility to be added only where it is needed.

In an alternative embodiment of the present invention, it is desired to start with a more flexible catheter shaft 11 and create zones of rigidity through the use of the present invention. Bands 15 can be created in the catheter shaft 11 and filled with a more rigid filler material 18, thereby creating a transition section 22 which is more rigid.

Figure 7:
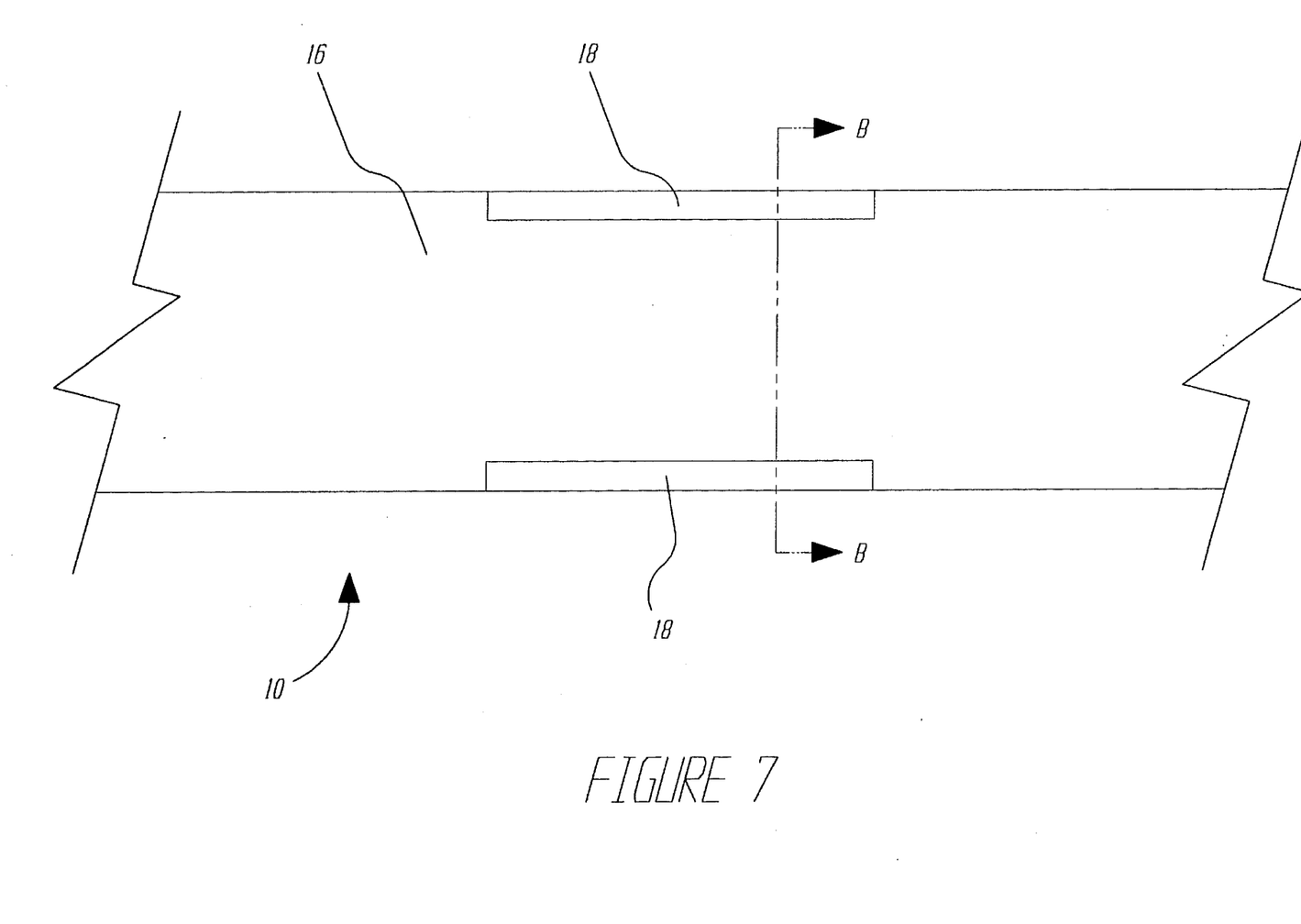
FIG. 7 is another embodiment of the present invention.
Figure 8:
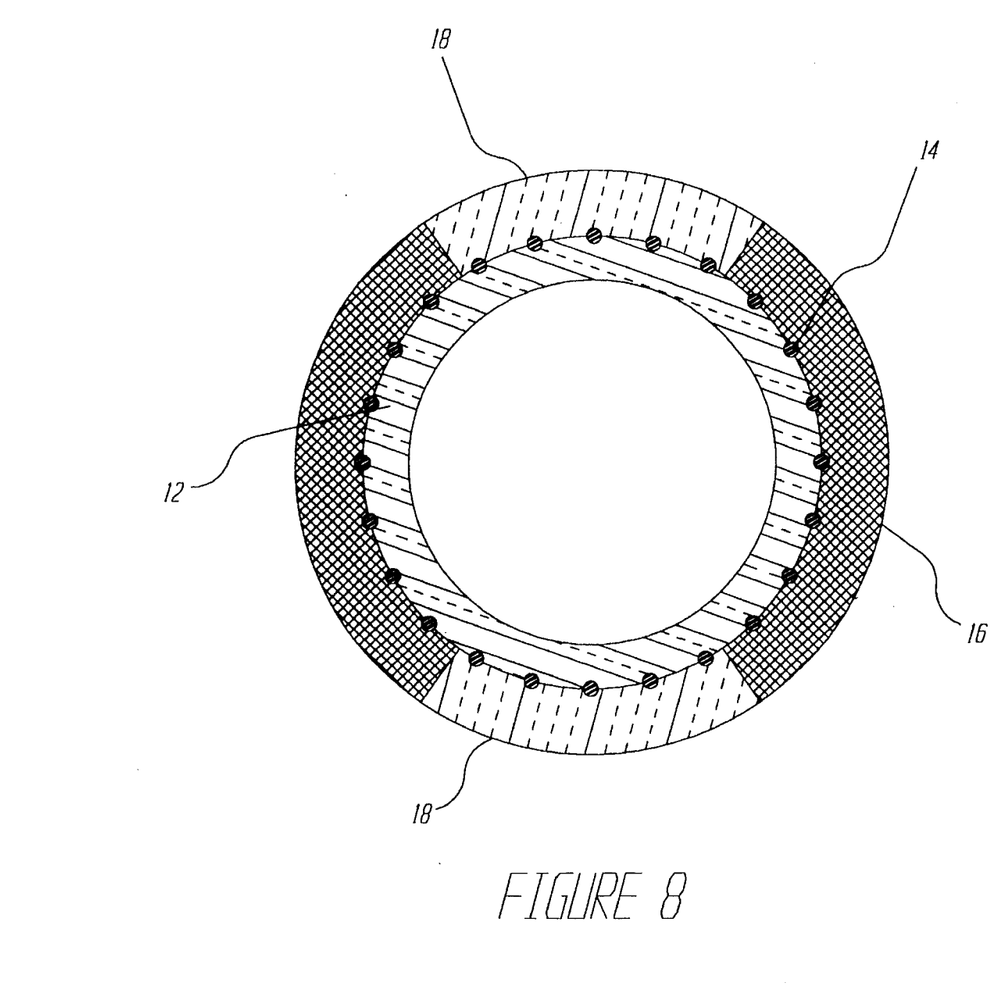
FIG. 8 is a cross section of FIG. 7 along line B—B.

FIGS. 7 & 8 represent another embodiment in which it is desired to create bending planes within the catheter shaft 11. This also can be accomplished through the use of the present invention. The catheter can be processed as described above, but instead of grinding the band 15 in a 360 degree manner, opposing sides of the catheter shaft 11 may be ground down and then filled with a more flexible filler material 18 to create a plane in which the transition element may bend. Alternatively, a flexible catheter shaft 11 can be ground down on opposing side and then filled with a more rigid filler material 18, to create planes in which the catheter may not bend.

In another embodiment of the present invention, the filler material 18 may be a composite or a blend of two different substances. Specifically, it may be comprised of a polymer tube which has a spring coil embedded therein to impart different flexibility in that section. It may also be comprised of two or more polymer sections that have physical properties that are different from each other and from the catheter shaft 11.

Although the present invention is described in terms of the preferred embodiment above, it should be noted that alterations and modifications to this invention will be possible without departing from the spirit and scope of this invention.

What is claimed is:

1. An intravascular guiding catheter which comprises:
   a) a flexible inner tube;
   b) a support member coupled to said inner tube;
   c) an outer tube congruent to said inner tube, having a proximal section, a transition section, and a distal section;
   d) wherein the transition section, located between the proximal and distal sections of said outer tube, is comprised of a material having different physical properties than the material of said proximal and distal sections; and
   e) said proximal and distal sections being comprised of materials having the same physical properties.

2. The catheter of claim 1 further comprising a primary bend wherein the transition section is located at the primary bend.

3. The catheter of claim 2 further comprising a second transition section located between the proximal and first transition sections of the outer tube and a secondary bend wherein the second transition section is located at the second bend.

4. The catheter of claim 3 in which said second transition section is comprised of a material which is more rigid than said proximal and distal section material.

5. The catheter of claim 2 wherein the transition section is comprised of a material which is more flexible than said proximal and distal section material.

6. The catheter of claim 1 in which said transition section is comprised of a material which is more flexible than said proximal and distal section materials.

7. The catheter of claim 1 in which said transition section is comprised of a material which is more rigid than said proximal and distal section materials.

8. The catheter of claim 1 in which said inner tube is made of polytetrafluoroethylene.

9. The catheter of claim 1 in which said support member comprises metal fibers wound about said inner tube.

10. The catheter of claim 1 in which said proximal, transition, and distal section materials are made of a polyether block-amide.

11. The catheter of claim 1 in which said transition section is placed 360 degrees around the inner tube and support member.

12. The catheter of claim 1 in which said transition section material is less than 360 degrees about said inner tube and support member, and wherein the remainder of said transition section comprises said proximal and distal section materials.

13. An intravascular guiding catheter for the placement of devices in the coronary arteries, comprising:
   a) an inner tube;
   b) an outer tube, having a proximal end and a distal end;
   c) a transition section located between the proximal and distal ends of said outer tube and wherein the transition section is less than 360° about said inner tube;
   d) said transition section being comprised of a material having different physical properties than said outer tube;
   e) said transition section creating bending planes within the catheter shaft, such that the catheter has the ability to bend in one plane but resists bending in another plane.

14. An intravascular catheter which comprises:
   a) an inner tube;
   b) a support member coupled to said inner tube;
   c) an outer tube congruent to said inner tube, having a proximal section, a transition section, and a distal section;
   d) wherein said transition section, located between said proximal and distal sections, is comprised of a material which is more flexible than the material of said proximal section and which is more flexible than the material of said distal section.

15. An intravascular catheter which comprises:
   a) an inner tube;
   b) a support member coupled to said inner tube;
   c) an outer tube congruent to said inner tube, having a proximal section, a transition section, and a distal section;
   d) wherein said transition section, located between said proximal and distal sections, is comprised of a material which is less flexible than the material of said proximal section and which is less flexible than the material of said distal section.

* * * * *

UNITED STATES PATENT AND TRADEMARK OFFICE
CERTIFICATE OF CORRECTION

PATENT NO. : 5,569,218

DATED : October 29, 1996

INVENTOR(S): BERG

It is certified that error appears in the above-identified patent and that said Letters Patent is hereby corrected as shown below:

Title page,

Item [56], References Cited, FOREIGN PATENT DOCUMENTS, insert

--0555088    10/1993    European Pat. Off.--

At column 4, line 4, "67 D" should be --67D--; at lines 4-5, "67 D" should be --67D--; at lines 5-6, "40-70 D" should be --40-70D--; at line 7, "35 D" should be --35D-- (both occurrences); at line 8, "25-72 D" should be --25-72D--; at line 12, "8 F" should be --8F--; at line 34, "35-40 D" should be --35-40D--.

Signed and Sealed this

Sixth Day of April, 1999

Attest:

Attesting Officer

Q. TODD DICKINSON

Acting Commissioner of Patents and Trademarks